(12) United States Patent
Sun et al.

(10) Patent No.: US 11,954,860 B2
(45) Date of Patent: Apr. 9, 2024

(54) IMAGE MATCHING METHOD AND DEVICE, AND STORAGE MEDIUM

(71) Applicant: Infervision Medical Technology Co., Ltd., Beijing (CN)

(72) Inventors: Mengmeng Sun, Beijing (CN); Shaokang Wang, Beijing (CN); Kuan Chen, Beijing (CN)

(73) Assignee: Infervision Medical Technology Co., Ltd., Beijing (CN)

( * ) Notice: Subject to any disclaimer, the term of this patent is extended or adjusted under 35 U.S.C. 154(b) by 458 days.

(21) Appl. No.: 17/398,790

(22) Filed: Aug. 10, 2021

(65) Prior Publication Data

US 2021/0366121 A1 Nov. 25, 2021

Related U.S. Application Data

(63) Continuation of application No. PCT/CN2020/094875, filed on Jun. 8, 2020.

(30) Foreign Application Priority Data

Oct. 21, 2019 (CN) .......................... 201911001697.3

(51) Int. Cl.
*G06T 7/00* (2017.01)
*A61B 6/03* (2006.01)
(Continued)

(52) U.S. Cl.
CPC .............. *G06T 7/0016* (2013.01); *G06T 7/33* (2017.01); *G06T 7/38* (2017.01); *A61B 6/032* (2013.01);
(Continued)

(58) Field of Classification Search
CPC ............ G06T 7/0016; G06T 7/33; G06T 7/38
See application file for complete search history.

(56) References Cited

U.S. PATENT DOCUMENTS 8,848,990 B2 * 9/2014 Xue .......................... G06T 7/30
382/128
2005/0135707 A1 * 6/2005 Turek ........................ G06T 7/38
382/128
(Continued)

FOREIGN PATENT DOCUMENTS

CN 101616310 A 12/2009
CN 103927746 A 7/2014
(Continued)

OTHER PUBLICATIONS

Extended European Search Report issued in counterpart European Patent Application No. 20880082.1, dated Apr. 8, 2022.
(Continued)

*Primary Examiner* — David Bilodeau
(74) *Attorney, Agent, or Firm* — Westbridge IP LLC (57) ABSTRACT

Disclosed are an image matching method, an image matching device, and a storage medium. A first image sequence and a second image sequence are acquired, and thus a first object and a second object are reconstructed and generated based on the first image sequence and the second image sequence respectively. The registration of the first object and the second object are further performed, and a mapping relationship obtained according to a registration result may indicate a correspondence between image frames in the first image sequence and image frames in the second image sequence. Compared with setting a difference value artificially, obtaining the correspondence between image frames in the first image sequence and image frames in the second image sequence by using the image matching method improves the matching accuracy.

13 Claims, 4 Drawing Sheets

(51) Int. Cl.
*G06T 7/33* (2017.01)
*G06T 7/38* (2017.01)

(52) U.S. Cl.
CPC ............ *G06T 2207/10016* (2013.01); *G06T 2207/10081* (2013.01); *G06T 2207/30096* (2013.01)

(56) References Cited

U.S. PATENT DOCUMENTS

| | | | | |
|---|---|---|---|---|
| 2014/0072196 | A1* | 3/2014 | Hwang | G06T 7/0016 382/130 |
| 2018/0137651 | A1* | 5/2018 | Levinshtein | G06T 9/20 |
| 2019/0056498 | A1* | 2/2019 | Sonn | G01S 17/931 |
| 2019/0197689 | A1* | 6/2019 | Chen | G06V 40/197 |
| 2019/0392602 | A1* | 12/2019 | Lloyd | G06T 7/73 |

FOREIGN PATENT DOCUMENTS

| | | |
|---|---|---|
| CN | 104750951 A | 7/2015 |
| CN | 104881568 A | 9/2015 |
| CN | 106157282 A | 11/2016 |
| CN | 106815832 A | 6/2017 |
| CN | 106934807 A | 7/2017 |
| CN | 107292872 A | 10/2017 |
| CN | 107454389 A | 12/2017 |
| CN | 107465940 A | 12/2017 |
| CN | 107595390 A | 1/2018 |
| CN | 109035234 A | 12/2018 |
| CN | 110021025 A | 7/2019 |
| CN | 110766735 A | 2/2020 |

OTHER PUBLICATIONS

Faber et al., Spatial and Temporal Registration of Cardiac SPECT and MR Images: Methods and Evaluation, Cardiac Radiology, vol. 179, No. 3, pp. 857-861, dated Jan. 1, 1991.

First Office Action issued in counterpart Chinese Patent Application No. 201911001697.3, dated Apr. 16, 2020.

International Search Report issued in corresponding PCT Application No. PCT/CN2020/094875, dated Aug. 27, 2020.

\* cited by examiner

IMAGE MATCHING METHOD AND DEVICE, AND STORAGE MEDIUM

CROSS-REFERENCE TO RELATED APPLICATIONS

The present application is a continuation application of International Application No. PCT/CN2020/094875 filed on Jun. 8, 2020, which claims priority to Chinese Patent Application No. 201911001697.3 filed on Oct. 21, 2019. Both applications are incorporated herein by reference in their entireties.

TECHNICAL FIELD

The present application relates to the technical field of information processing, in particular to an image matching method, an image matching device, and a storage medium.

BACKGROUND

In the field of medical imaging, it is necessary to compare image frames in medical image sequences photographed for multiple times to make a more accurate diagnosis. For example, after a patient has been diagnosed with a lesion by an image for a first time, it is diagnosed by a clinician that there is no need to deal with it immediately, and the patient is required to be reviewed within a certain period of time. A follow-up image will be taken for the patient during the review, and the clinician will make a diagnosis again based on comparison of the lesions in the images photographed for two times to determine the condition of the patient. The image photographed each time is an image sequence (such as CT image sequence) including a plurality of image frames, so it is necessary to determine a correspondence between the image frames in the two image sequences during comparing and viewing. In general, in different image sequences, the image frames including a same region (for a CT image sequence, the region may be a scanning layer) of a photographed tissue are called corresponding image frames, and the correspondence is a correspondence between the image frames. For example, if a scanning layer included in the third frame of an image sequence photographed last time correspondingly appears in the fifth frame of an image sequence photographed this time, then the third frame of the image sequence photographed last time is corresponding to the fifth frame of the image sequence photographed this time.

At present, the method to determine the correspondence between image frames is to set a difference value between numbers of the image frames artificially according to experience, so as to view two image frames whose numbers conform to the difference value. For example, based on an observation of a tissue (such as a lesion) artificially according to experience, it is determined that the third frame of the image sequence photographed last time is corresponding to the fifth frame of the image sequence photographed this time, then the difference value is set to 2. According to the difference value, the eighth frame of the image sequence photographed this time is corresponding to the sixth frame of the image sequence photographed last time. However, there are differences between the image sequences photographed each time, for example, a change in the patient's internal organs (such as respiratory motion) may cause a large difference in a distribution of the image frames of the organs in different image sequences, so the difference value applicable to two image frames is not necessarily applicable to all image frames in two image sequences. For example, the scanning layer included in the eighth frame of the image sequence photographed this time is possibly different from that in the sixth frame of the image sequence photographed last time. Therefore, the accuracy of the correspondence between image frames obtained by setting a difference value artificially is low.

SUMMARY

In view of this, the present application provides an image matching method, apparatus and device, and a storage medium, to obtain a correspondence between image frames with high accuracy.

An image matching method includes: acquiring a first image sequence and a second image sequence, wherein the first image sequence and the second image sequence are image frame sequences acquired for a same object; acquiring a first object and a second object, wherein the first object is an object reconstructed using the first image sequence, and the second object is an object reconstructed using the second image sequence; performing registration of the first object and the second object to obtain a registration result, wherein the registration result includes a one-to-one correspondence between any pixel point on the first object and a pixel point on the second object; acquiring a mapping relationship according to the registration result, wherein the mapping relationship is configured to indicate a correspondence between an image frame in the first image sequence and an image frame in the second image sequence; and displaying a matching image frame correspondingly according to the mapping relationship in case of displaying a target image frame in the first image sequence, wherein the matching image frame is an image frame in the second image sequence corresponding to the target image frame, and the target image frame is any image frame in the first image sequence.

Alternatively, the acquiring a first image sequence and a second image sequence includes: receiving the first image sequence; and acquiring an image sequence having a same identification with the first image sequence from historical image sequences as the second image sequence.

Alternatively, the receiving the first image sequence includes: acquiring the first image sequence from an image sequence imaging device, in case of the image sequence imaging device generating the first image sequence.

Alternatively, the performing registration of the first object and the second object to obtain a registration result includes: dividing the first object and the second object into multiple parts respectively; pairing vertices of a first circumscribed polyhedron and a second circumscribed polyhedron to obtain matching points, wherein the first circumscribed polyhedron is a circumscribed polyhedron of each part obtained by dividing the first object, and the second circumscribed polyhedron is a circumscribed polyhedron of each part obtained by dividing the second object; determining a registration matrix equation according to the matching points; and solving the registration matrix equation by using a least square method to obtain the registration result.

Alternatively, the method further includes: acquiring first lesion information and second lesion information, wherein the first lesion information represents diagnosis information of a lesion obtained based on the first image sequence, and the second lesion information represents diagnosis information of a lesion obtained based on the second image sequence; and displaying contents of same items in the first lesion information and the second lesion information correspondingly.

Alternatively, the method further includes: acquiring a second frame identification, wherein the second frame identification is an identification of an image frame in which a lesion is located in the second image sequence; and determining a first frame identification according to the second frame identification and the mapping relationship, wherein the first frame identification is an identification of an image frame in which a lesion is located in the first image sequence, and acquisition time of the first image sequence is later than that of the second image sequence.

An image matching apparatus includes: an image sequence acquiring unit, configured to acquire a first image sequence and a second image sequence, wherein the first image sequence and the second image sequence are image frame sequences acquired for a same object; an object acquiring unit, configured to acquire a first object and a second object, wherein the first object is an object reconstructed using the first image sequence, and the second object is an object reconstructed using the second image sequence; a registration unit, configured to perform registration of the first object and the second object to obtain a registration result, wherein the registration result includes a one-to-one correspondence between any pixel point on the first object and a pixel point on the second object; a mapping relationship acquiring unit, configured to acquire a mapping relationship according to the registration result, wherein the mapping relationship is configured to indicate a correspondence between an image frame in the first image sequence and an image frame in the second image sequence; an image displaying unit, configured to display a matching image frame correspondingly according to the mapping relationship in case of displaying a target image frame in the first image sequence, wherein the matching image frame is an image frame in the second image sequence corresponding to the target image frame, and the target image frame is any image frames in the first image sequence.

Alternatively, the image sequence acquiring unit, configured to acquire a first image sequence and a second image sequence, includes: the image sequence acquiring unit configured to: receive the first image sequence; and acquire an image sequence having a same identification with the first image sequence from historical image sequences as the second image sequence.

Alternatively, the image sequence acquiring unit configured to receive the first image sequence includes: the image sequence acquiring unit configured to acquire the first image sequence from an image sequence imaging device, in case of the image sequence imaging device generating the first image sequence.

Alternatively, the registration unit, configured to perform registration of the first object and the second object to obtain a registration result, includes: the registration unit configured to: divide the first object and the second object into multiple parts respectively; pair vertices of a first circumscribed polyhedron and a second circumscribed polyhedron to obtain matching points, wherein the first circumscribed polyhedron is a circumscribed polyhedron of each part obtained by dividing the first object, and the second circumscribed polyhedron is a circumscribed polyhedron of each part obtained by dividing the second object; determine a registration matrix equation according to the matching points; and solve the registration matrix equation by using a least square method to obtain the registration result.

Alternatively, the apparatus further includes: a lesion information acquiring unit, configured to acquire first lesion information and second lesion information, wherein the first lesion information represents diagnosis information of a lesion obtained based on the first image sequence, and the second lesion information represents diagnosis information of a lesion obtained based on the second image sequence; and a lesion information displaying unit, configured to display contents of same items in the first lesion information and the second lesion information correspondingly.

Alternatively, the apparatus further includes: a second frame identification acquiring unit, configured to acquire a second frame identification, wherein the second frame identification is an identification of an image frame in which a lesion is located in the second image sequence; and a first frame identification acquiring unit, configured to determine a first frame identification according to the second frame identification and the mapping relationship, wherein the first frame identification is an identification of an image frame in which a lesion is located in the first image sequence, and acquisition time of the first image sequence is later than that of the second image sequence.

An image matching device includes a memory and a processor, and the memory is configured to store programs; and the processor is configured to execute the programs to implement steps of an image matching method described above.

A storage medium stores computer programs, and when executed by a processor, the computer programs cause the processor to implement steps of an image matching method described above.

It can be seen from the above technical solutions, according to the image matching method, apparatus and device, and the storage medium, provided by the present application, the first image sequence and the second image sequence are acquired, and thus the first object and the second object are reconstructed and generated based on the first image sequence and the second image sequence respectively. Since the first image sequence and the second image sequence are image frame sequences acquired for the same object, the first object and the second object are the results obtained by collecting the object, i.e., the first object and the second object have highly similar shapes. Accordingly, the registration of the first object and the second object are further performed to obtain a registration result, and then a mapping relationship obtained according to the registration result may indicate the correspondence between image frames in the first image sequence and image frames in the second image sequence. Furthermore, the method may display a target image frame and a matching image frame correspondingly according to the mapping relationship. In summary, compared with setting a difference value artificially, obtaining the correspondence between image frames in the first image sequence and image frames in the second image sequence by using the image matching method greatly improves the matching accuracy.

BRIEF DESCRIPTION OF DRAWINGS

In order to more clearly illustrate the technical solutions in embodiments of the present application or in prior art, a brief description of drawings required in the description of the embodiments or prior art are given below. Obviously, the drawings described below are only embodiments of the present application, and other drawings may be obtained according to the provided drawings for those of ordinary skill in the art without any creative effort.

DETAILED DESCRIPTION OF THE EMBODIMENTS

The technical solutions provided in the present application are applicable but not limited to medical images.

The technical solutions in the embodiments of the present application are described clearly and completely below in combination with the drawings provided in the embodiments of the present application. Obviously, the embodiments described herein are only a part of embodiments of the present application, and not all of the embodiments. Based on the embodiments in the present application, all other embodiments obtained by those of ordinary skill in the art without creative efforts shall fall within the protection scope of the present application.

Figure 1:
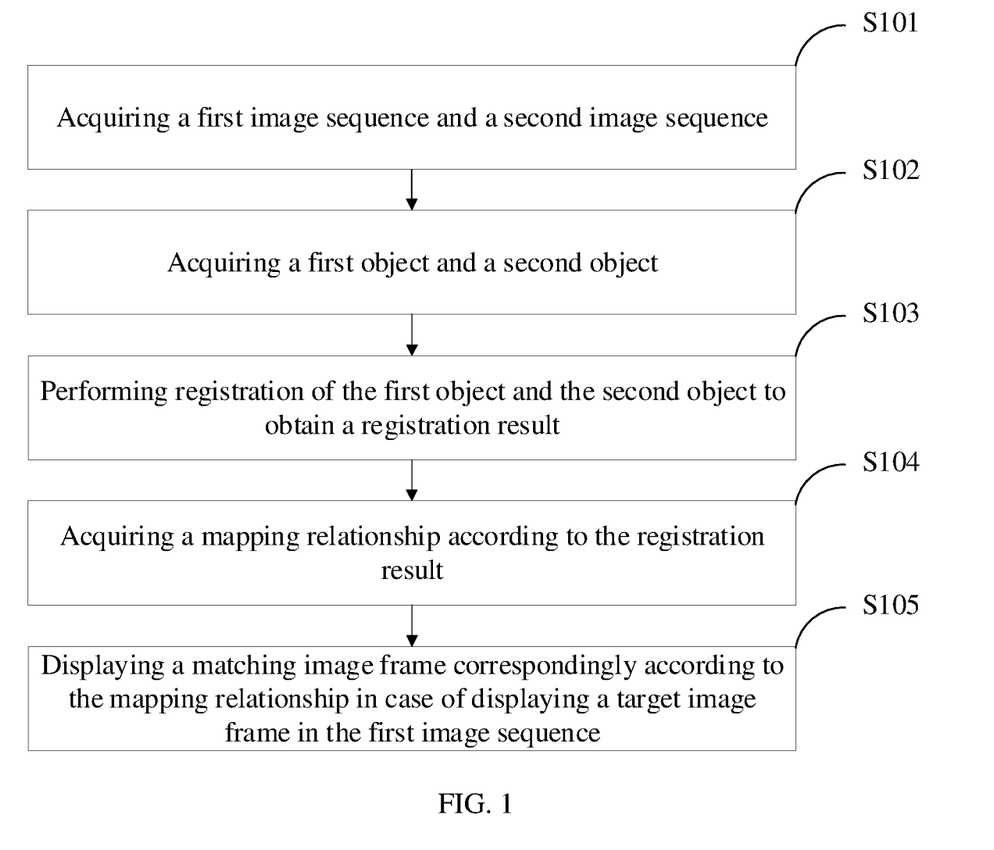
FIG. 1 is a schematic flowchart illustrating an image matching method according to an embodiment of the present application.

FIG. 1 is a flowchart illustrating an image matching method according to an embodiment of the present application, which specifically includes the following contents.

S101: acquiring a first image sequence and a second image sequence.

Specifically, each image sequence includes a plurality of successive image frames. The first image sequence and the second image sequence obtained in this step are image frame sequences acquired for a same object.

There may be multiple methods for acquiring the first image sequence and the second image sequence.

An optional acquiring method is to select the first image sequence and the second image sequence directly.

Specifically, taking a CT image sequence in medical images as an example, the first image sequence may be a follow-up CT image sequence of a patient, and the second image sequence may be a historical CT image sequence of the patient. The historical CT image sequence may include CT image sequences photographed for multiple times. It should be understood that, each image sequence is a CT image sequence photographed for a same part of the patient. At this time, the CT image sequences of the patient photographed for multiple times may be retrieved from PACS (Picture Archiving and Communication System) directly according to information of the patient, to perform a subsequent image matching method.

Alternatively, an embodiment of the present application provides a method for acquiring the first image sequence and the second image sequence automatically as follows:

receiving the first image sequence; and
acquiring an image sequence having a same identification with the first image sequence from historical image sequences as the second image sequence.

Alternatively, a method for receiving the first image sequence may include acquiring the first image sequence from an image sequence imaging device in case of the image sequence imaging device generating the first image sequence.

Specifically, this method may monitor the dynamics of an image sequence imaging device at the front end by directly connecting with the image sequence imaging device (such as a CT imaging device). When an image sequence is imaged, the image sequence sent by the imaging device is received automatically and used as the first image sequence.

Alternatively, a method for receiving the first image sequence may include automatically receiving the image sequence sent by the PACS device and using the image sequence as the first image sequence when a new image sequence is stored. This method may monitor the storage dynamics of the image sequence by connecting with the PACS directly.

In the method for acquiring the first image sequence and the second image sequence automatically, it should be understood that, there is a unique identification for each image sequence, and the identification represents a user that the image sequence belongs to. Alternatively, the identification may include personal information (name, gender, age, etc.) of the patient that the first image sequence belongs to and an image type (abdominal CT, chest CT, head CT, etc.).

The historical image sequences are stored in the PACS, each historical image sequence is corresponding to a unique identification, and the historical image sequences are image sequences of the same type photographed at different time points.

Alternatively, other acquisition conditions (such as photographing time) may also be preset to further filter an expected second image sequence from multiple groups of historical image sequences.

Taking a follow-up image sequence of a patient as an example, a follow-up CT image sequence of the patient is photographed under the guidance of a clinician, and this method acquires the follow-up CT image sequence directly from a CT device as the first image sequence. At the same time, the personal information (name: Zhang San, gender: male, age: 30) of the follow-up CT image sequence and the image type (chest CT) are obtained. Furthermore, a historical CT image sequence conforming to the above personal information and the image type is acquired from the PACS as the second image sequence. Furthermore, a filtering condition may be preset as an acquisition time of two years, then, the historical CT image sequences conforming to the above personal information and the image type are acquired from the PACS, and the historical CT image sequence(s) within two years is filtered from the above historical CT image sequences and set as the second image sequence(s).

S102: acquiring a first object and a second object.

It can be seen from the above description, the first image sequence and the second image sequence are image frame sequences acquired for the same object, so the first object is an object reconstructed by using the first image sequence, and the second object is an object reconstructed by using the second image sequence. For example, based on chest CT image sequences of the patient Zhang San, for the same object (such as the lung) acquired for two times, both the first object and the second object obtained by reconstructing are three-dimensional reconstruction results of the patient Zhang San's lung.

Alternatively, in this step, a traditional threshold method, watershed method, or segmentation algorithm based on deep learning may be used to obtain an object region, and then the object region may be reconstructed to obtain the first object and the second object.

S103: performing registration of the first object and the second object to obtain a registration result.

It should be understood that, the first object and the second object are for the same object, so the first object and the second object have highly similar shapes. Moreover, points of the first object may be represented by coordinates in a space established based on the first image sequence, and points of the second object may be represented by coordinates in a space established based on the second image sequence. Thus, registration of all the points in the first object and the second object may be performed based on the transformation of the spatial coordinates.

Alternatively, registration of any point in the first object and a point in the second object at the same location of the object may be performed according to the spatial coordinate transformation method. The registration result of the first object and the second object may be obtained by performing registration of multiple points.

S104: acquiring a mapping relationship according to the registration result.

Specifically, the registration result represents a registration relationship between the first object and the second object, and the registration relationship is a spatial mapping relationship between the points in the first object and the second object (for any real point in the object, the registration relationship is a correspondence between a coordinate point of the real point in the first object and a coordinate point of the real point in the second object). Since an image frame is a frame in an image sequence, the first object corresponds to multiple image frames in the first image sequence, and the second object corresponds to multiple image frames in the second image sequence. Therefore, in this step, by the transformation of a spatial mapping relationship and a physical mapping relationship, a correspondence between each image frame in the first image sequence and each image frame in the second image sequence may be obtained according to the registration result.

It should be noted that the transformation of the spatial mapping relationship and the physical mapping relationship may refer to the existing transformation method, which is not limited in the embodiments of the present application.

Alternatively, each image frame in an image sequence is corresponding to a frame identification, and the frame identification of the image frame represents the location of the image frame in the image sequence. Therefore, the correspondence may be stored as a correspondence table of the frame identifications of the image frames.

S105: displaying a matching image frame correspondingly according to the mapping relationship in case of displaying a target image frame in the first image sequence.

The target image frame is any image frame in the first image sequence, and the matching image frame is an image frame in the second image sequence corresponding to the target image frame.

Alternatively, the case for displaying the target image frame in the first image sequence may include displaying any image frame in the first image sequence based on a user's operation, and this image frame is the target image frame. At this time, the image frame corresponding to the target image frame, i.e., the matching image frame, may be acquired from the second image sequence according to the above mapping relationship obtained by the method. Furthermore, the target image frame and the matching image frame are displayed.

For example, after obtaining the follow-up image sequence of a patient, the clinician needs to compare the follow-up image sequence and the previous image sequence, to obtain a more accurate diagnosis. At this time, the clinician may choose to display any image frame in the follow-up image sequence. The matching image frame in the previous image sequence corresponding to the image frame may be determined based on the mapping relationship. Based on this, the image frame and the matching image frame of the image frame may be displayed at the same time.

It should be noted that, the specific implementation of the display may include connecting with a preset display interface, which may provide users with linkage to view each image frame, and has the function of operating the image frame (zoom in, zoom out, translation, etc.).

It can be seen from the above technical solutions, according to the image matching method, apparatus and device, and the storage medium, provided by the present application, the first image sequence and the second image sequence are acquired, and thus the first object and the second object are reconstructed and generated based on the first image sequence and the second image sequence respectively. Since the first image sequence and the second image sequence are image frame sequences acquired for the same object, the first object and the second object are the results obtained by collecting the object, i.e., the first object and the second object have highly similar shapes. Accordingly, the registration of the first object and the second object are further performed to obtain a registration result, and then a mapping relationship obtained according to the registration result may indicate the correspondence between image frames in the first image sequence and image frames in the second image sequence. Furthermore, the method may display a target image frame and a matching image frame correspondingly according to the mapping relationship. In summary, compared with setting a difference value artificially, obtaining the correspondence between image frames in the first image sequence and image frames in the second image sequence by using the image matching method greatly improves the matching accuracy.

Figure 2:
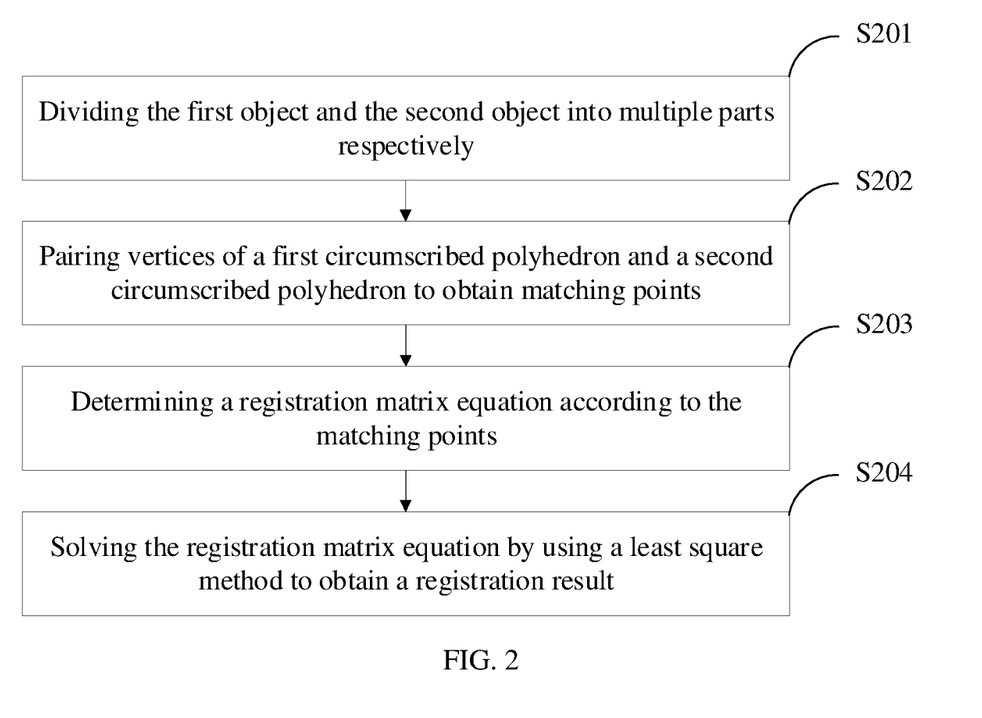
FIG. 2 is a schematic flowchart illustrating a method for performing registration of a first object and a second object according to an embodiment of the present application.

FIG. 2 is a schematic flowchart illustrating a method for performing registration of a first object and a second object according to an embodiment of the present application. In an embodiment of the present application, the registration process of the first object and the second object is described by taking the first image sequence and the second image sequence as chest CT image sequences and the object as a lung as an example. Specifically, it may include the following contents.

S201: dividing the first object and the second object into multiple parts respectively.

The first image sequence is a follow-up CT image sequence recorded as DICOM1, and the second image sequence is a previous CT image sequence recorded as DICOM2. The first object (lung) is represented as LUNG1, and the second object (lung) is represented as LUNG2.

In this step, the LUNG1 and the LUNG2 may be divided into k equal parts along the long axis of the human body respectively. It should be understood that, since the LUNG1 and the LUNG2 are the same object, the shapes of the ith ($1 \le i \le k$) part of the LUNG1 and the ith part of the LUNG2 are highly similar.

S202: pairing vertices of a first circumscribed polyhedron and a second circumscribed polyhedron to obtain matching points.

Specifically, the circumscribed polyhedrons of the multiple parts divided from the first object and the second object are calculated. The first circumscribed polyhedron may be the smallest bounding cube for each part divided from the first object LUNG1, and the second circumscribed polyhedron may be the smallest bounding cube for each part divided from the second object LUNG2. It can be seen from above description, the ith first circumscribed polyhedron and the ith second circumscribed polyhedron are the same part of the same object, so the vertices of each first circumscribed polyhedron may be paired with the corresponding vertices of the second circumscribed polyhedron to obtain multiple matching points.

For example, the number of the first circumscribed polyhedrons is k, recorded as $LUNG1_1, \ldots, LUNG1_2, \ldots, LUNG1_k$ and the number of the second circumscribed polyhedrons is k, recorded as $LUNG2_1, LUNG2_2, \ldots, LUNG2_k$.

Furthermore, vertices of $LUNG1_1$ and $LUNG2_1$, $LUNG1_2$ and $LUNG2_2$, $\ldots$, $LUNG1_k$ and $LUNG2_k$ are paired respectively to obtain 8 k pairs of matching points. Taking $LUNG1_1$ and $LUNG2_1$ as an example, there are 8 vertices in $LUNG1_1$, the 8 vertices are paired with 8 vertices in the corresponding locations in $LUNG2_1$, so 8 pairs of matching points of $LUNG1_1$ and $LUNG2_1$ are obtained.

S203: determining a registration matrix equation according to the matching points.

Specifically, coordinates of the 8 k vertices in each object may be arranged into an 8 k×3 vertex matrix V, as follows:

$$V = \begin{bmatrix} x_{11}^T \\ x_{12}^T \\ \ldots \\ x_{17}^T \\ x_{18}^T \\ x_{21}^T \\ \vdots \\ x_{k8}^T \end{bmatrix}$$

Here, $x_{ij}$ represents the jth ($1 \leq j \leq 8$) vertex coordinate of the ith ($1 \leq i \leq k$) circumscribed polyhedron of the object.

In this step, the vertex matrix of the first object is represented as $V^{tar}$, the element in row r, column 1 ($1 \leq r \leq 8$ k) of the vertex matrix $V^{tar}$ is represented as $V_{r,1}^{tar}$, i.e., the x-coordinate of the rth vertex in $V^{tar}$. The element in row r, column 2 of the vertex matrix $V^{tar}$ is represented as $V^{tar}_{r,2}$, i.e., the y-coordinate of the rth vertex in $V^{tar}$. The element in row r, column 3 of the vertex matrix $V^{tar}$ is represented as $V^{tar}_{r,3}$, i.e., the z-coordinate of the rth vertex in $V^{tar}$. Based on the above representations, the vertex matrix W of the first object may be obtained by transforming the matrix form of $V^{tar}$ as follows:

$$W = \begin{bmatrix} V_{1,1}^{tar} \\ V_{1,2}^{tar} \\ V_{1,3}^{tar} \\ V_{2,1}^{tar} \\ \ldots \\ V_{8k,3}^{tar} \end{bmatrix}$$

The vertex matrix of the second object is represented as $V^{org}$, and the rth row of the vertex matrix $V^{org}$ is represented as $V_r^{org}$.

The mapping relationship may be assumed to be a 12-dimensional vector T, and $T = [A_1 \; b_1 \; A_2 \; b_2 \; A_3 \; b_3]^T$, wherein $A_1 = [a_{11} \; a_{12} \; a_{13}]$, $A_2 = [a_{21} \; a_{22} \; a_{23}]$, and $A_3 = [a_{31} \; a_{32} \; a_{33}]$. The registration of the first object and the second object are performed based on the coordinate transformation, and a registration matrix equation is as follows:

$$\begin{bmatrix} V_{1,1}^{tar} \\ V_{1,2}^{tar} \\ V_{1,3}^{tar} \\ V_{2,1}^{tar} \\ \vdots \\ V_{8k,3}^{tar} \end{bmatrix} \begin{bmatrix} V_1^{org} & 1 & 0 & 0 & 0 & 0 \\ 0 & 0 & V_1^{org} & 1 & 0 & 0 \\ 0 & 0 & 0 & 0 & V_1^{org} & 1 \\ \vdots & \vdots & \vdots & \vdots & \vdots & \vdots \\ V_{8k}^{org} & 1 & 0 & 0 & 0 & 0 \\ 0 & 0 & V_{8k}^{org} & 1 & 0 & 0 \\ 0 & 0 & 0 & 0 & V_{8k}^{org} & 1 \end{bmatrix} \begin{bmatrix} A_1^T \\ b_1 \\ A_2^T \\ b_2 \\ A_3^T \\ b_3 \end{bmatrix}$$

S204: solving the registration matrix equation by using a least square method to obtain a registration result.

Specifically, the mapping relationship formula $T = [A_1 \; b_1 \; A_2 \; b_2 \; A_3 \; b_3]^T$ may be calculated and obtained by solving the registration matrix equation using a least square method.

The mapping relationship formula is obtained by using a coordinate transformation for 8 k matching points of the first object and the second object, so the mapping relationship formula also may represent a registration relationship of two points in the same location of the first object and the second object. That is, the coordinate of the matching point, located in the second object, of any point in the first object, may be calculated by using the coordinate of the point in the first object and the mapping relationship formula.

Alternatively, the method may also display lesion information of the first image sequence and the second image sequence, and the displaying method may specifically include the following contents.

Firstly, first lesion information and second lesion information are acquired.

The first lesion information represents diagnosis information of a lesion obtained based on the first image sequence, and the second lesion information represents diagnosis information of a lesion obtained based on the second image sequence.

There are multiple information items included in each lesion information. For example, the information items of diagnosis information may be physical diagnosis information (size, shape, range, etc.) of the lesion and manual diagnosis information (property of the lesion, degree of the lesion, etc.). Each information item of the diagnosis information may be acquired from the PACS, or acquired from other information systems such as a diagnosis system according to the identification of the image sequences.

It should be understood that, the first lesion information and the second lesion information may include the same information items, in order to facilitate a user to intuitively compare various information of the first image sequence and the second image sequence, contents of the same items in the first lesion information and the second lesion information may be further displayed respectively.

Alternatively, a correspondence table of the information items may be generated, in which the same items are arranged correspondingly, and different items are arranged separately. The correspondence table may be displayed in the case of displaying the first lesion information of the first image sequence based on an operation of a user.

In summary, this technical solution further provides a displaying method, which may display two image frames with a mapping relationship in the first image sequence and the second image sequence at the same time, so as to facilitate a user to compare and observe images in the image frames. In addition, the technical solution can display the same items in the first lesion information and the second lesion information correspondingly, and multiple diagnosis results may be simply and clearly compared to obtain the changing information of the lesion, thus providing a user with a basis for a further diagnosis and further improving the accuracy of the diagnosis.

After receiving the first image sequence, in order to avoid the low efficiency caused by a user looking for a lesion in multiple image frames, the method further includes the following contents.

Acquiring a second frame identification, and determining a first frame identification according to the second frame identification and the mapping relationship.

The second frame identification is an identification of an image frame in which a lesion is located in the second image sequence. The first frame identification is an identification of an image frame in which a lesion is located in the first image sequence. It should be noted that acquisition time of the first image sequence is later than that of the second image sequence.

It should be understood that, the second image sequence is a historical image sequence, and the specific location of the lesion in the second image sequence has been obtained through the diagnosis of the user, i.e., the identification of the image frame where the lesion is located in the second image sequence. Moreover, since the correspondence between each image frame in the first image sequence and each image frame in the second image sequence is obtained in the above embodiments, according to the second frame identification, the image frame corresponding to the image frame indicated by the second frame identification may be searched from the first image sequence, and the frame identification of the image frame may be obtained as a first frame identification.

It should be understood that, the lesion may be viewed by directly selecting the image frame indicated by the first frame identification. It is not necessary to manually view all image frames one by one to obtain the image frame where the lesion is located, thus improving work efficiency.

It should be noted that, the method may be applied to intelligent electronic devices, such as mobile phone, IPAD, computer, etc., and may be run in the form of independent software, in this case, it is necessary to connect with the PACS, other information systems or display systems, etc. Alternatively, it may be embedded into an existing system, such as the PACS. Moreover, the method may store the results of the mapping relationship, the first lesion information, the second lesion information, or the correspondence table obtained in the above embodiments.

The embodiments of the present application further provide an image matching apparatus. The image matching apparatus provided in the embodiments of the present application is described below, and the image matching apparatus described below and the image matching method described above may be correspondingly referred to each other.

Figure 3:
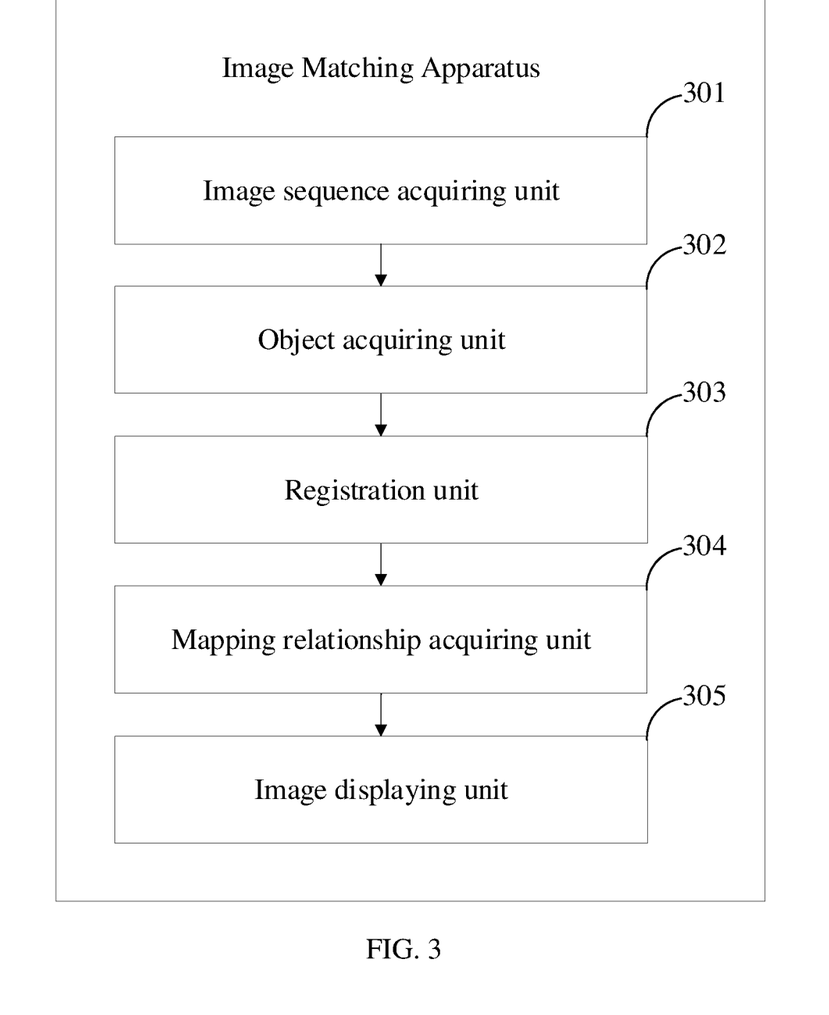
FIG. 3 is a schematic structural diagram illustrating an image matching apparatus according to an embodiment of the present application.

FIG. 3 is a schematic structural diagram illustrating an image matching apparatus according to an embodiment of the present application, as shown in FIG. 3, the apparatus may include: an image sequence acquiring unit 301, configured to acquire a first image sequence and a second image sequence, wherein the first image sequence and the second image sequence are image frame sequences acquired for a same object; an object acquiring unit 302, configured to acquire a first object and a second object, wherein the first object is an object reconstructed using the first image sequence, and the second object is an object reconstructed using the second image sequence; a registration unit 303, configured to perform registration of the first object and the second object to obtain a registration result, wherein the registration result includes a one-to-one correspondence between any pixel point on the first object and a pixel point on the second object; a mapping relationship acquiring unit 304, configured to acquire a mapping relationship according to the registration result, wherein the mapping relationship is configured to indicate a correspondence between an image frame in the first image sequence and an image frame in the second image sequence; and an image displaying unit 305, configured to display a matching image frame correspondingly according to the mapping relationship in case of displaying a target image frame in the first image sequence, wherein the matching image frame is an image frame in the second image sequence corresponding to the target image frame, and the target image frame is any image frame in the first image sequence.

Alternatively, the image sequence acquiring unit, configured to acquire a first image sequence and a second image sequence, includes: the image sequence acquiring unit specifically configured to: receive the first image sequence; and acquire an image sequence having a same identification with the first image sequence from historical image sequences as the second image sequence.

Alternatively, the image sequence acquiring unit configured to receive the first image sequence, includes: the image sequence acquiring unit specifically configured to acquire the first image sequence from an image sequence imaging device, in case of the image sequence imaging device generating the first image sequence.

Alternatively, the registration unit, configured to perform registration of the first object and the second object to obtain a registration result, includes: the registration unit specifically configured to: divide the first object and the second object into multiple parts respectively; pair vertices of a first circumscribed polyhedron and a second circumscribed polyhedron to obtain matching points, wherein the first circumscribed polyhedron is a circumscribed polyhedron of each part obtained by dividing the first object, and the second circumscribed polyhedron is a circumscribed polyhedron of each part obtained by dividing the second object; determine a registration matrix equation according to the matching points; and solve the registration matrix equation by using a least square method to obtain the registration result.

Alternatively, the apparatus further includes: a lesion information acquiring unit, configured to acquire first lesion information and second lesion information, wherein the first lesion information represents diagnosis information of a lesion obtained based on the first image sequence, and the second lesion information represents diagnosis information of a lesion obtained based on the second image sequence; and a lesion information displaying unit, configured to display contents of same items in the first lesion information and the second lesion information correspondingly.

Alternatively, the apparatus further includes: a second frame identification acquiring unit, configured to acquire a second frame identification, wherein the second frame identification is an identification of an image frame in which a lesion is located in the second image sequence; and a first frame identification acquiring unit, configured to determine a first frame identification according to the second frame identification and the mapping relationship, wherein the first frame identification is an identification of an image frame in which a lesion is located in the first image sequence, and acquisition time of the first image sequence is later than that of the second image sequence.

Figure 4:
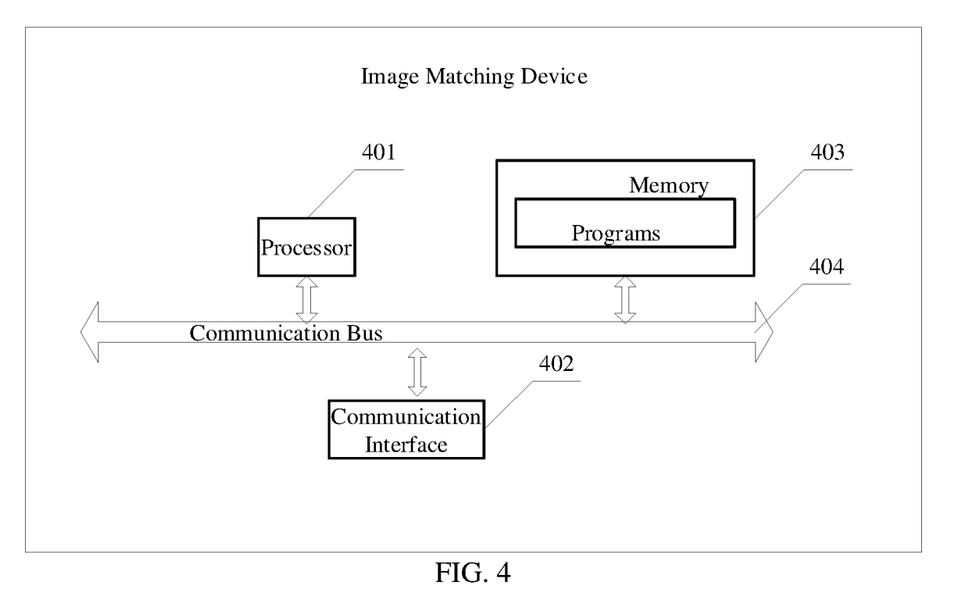
FIG. 4 is a schematic structural diagram illustrating an image matching device according to an embodiment of the present application.

The embodiments of the present application further provide an image matching device, referring to FIG. 4, which is a schematic structural diagram illustrating the image matching device. The device may include: at least one processor 401, at least one communication interface 402, at least one memory 403 and at least one communication bus 404.

In an embodiment of the present application, the number of the processor 401, the communication interface 402, the memory 403 or the communication bus 404 is at least one, and the processor 401, the communication interface 402 and the memory 403 communicate with each other by the communication bus 404.

The processor 401 may be a Central Processing Unit (CPU), or an Application Specific Integrated Circuit (ASIC), or one or more integrated circuits configured to implement embodiments of the present application, etc.

The memory 403 may include high-speed RAM memory, and may also include non-volatile memory, etc., such as at least one disk memory.

The memory is configured to store programs, the processor is configured to call the programs stored in the memory, and the programs may be used for: acquiring a first image sequence and a second image sequence, wherein the first image sequence and the second image sequence are image frame sequences acquired for a same object; acquiring a first object and a second object, wherein the first object is an object reconstructed using the first image sequence, and the second object is an object reconstructed using the second image sequence; performing registration of the first object and the second object to obtain a registration result, wherein the registration result includes a one-to-one correspondence between any pixel point on the first object and a pixel point on the second object; acquiring a mapping relationship according to the registration result, wherein the mapping relationship is configured to indicate a correspondence between an image frame in the first image sequence and an image frame in the second image sequence; and displaying a matching image frame correspondingly according to the mapping relationship in case of displaying a target image frame in the first image sequence, wherein the matching image frame is an image frame in the second image sequence corresponding to the target image frame, and the target image frame is any image frame in the first image sequence.

Alternatively, the detailed functions and extension functions of the programs may refer to the description above.

The embodiments of the present application further provide a storage medium, the storage medium may store programs suitable for the processor to execute, and the programs may be used for: acquiring a first image sequence and a second image sequence, wherein the first image sequence and the second image sequence are image frame sequences acquired for a same object; acquiring a first object and a second object, wherein the first object is an object reconstructed using the first image sequence, and the second object is an object reconstructed using the second image sequence; performing registration of the first object and the second object to obtain a registration result, wherein the registration result includes a one-to-one correspondence between any pixel point on the first object and a pixel point on the second object; acquiring a mapping relationship according to the registration result, wherein the mapping relationship is configured to indicate a correspondence between an image frame in the first image sequence and an image frame in the second image sequence; and displaying a matching image frame correspondingly according to the mapping relationship in case of displaying a target image frame in the first image sequence, wherein the matching image frame is an image frame in the second image sequence corresponding to the target image frame, and the target image frame is any image frame in the first image sequence.

Alternatively, the detailed functions and extension functions of the programs may refer to the description above.

Finally, it should be also noted that, in the present application, relationship terms such as first and second are used only to distinguish one entity or operation from another, and do not necessarily require or imply that any such actual relationship or order exists between these entities or operations. Moreover, terms "comprise", "include" or any other variations of them are intended to cover a non-exclusive inclusion, so that a process, a method, an object or a device including a series of elements not only include those elements, but also include other elements not explicitly listed, or also include inherent elements for the process, the method, the object or the device. Unless stated otherwise, defining in a sentence of "include a . . . " element does not exclude a case that there is also another same element in the process, the method, the object or the device including the described element.

The embodiments in the present application are described in a progressive manner, each embodiment focuses on differences from the other embodiments, and the same or similar parts between the embodiments may be referred to each other.

The description of the embodiments disclosed above enables a person skilled in the art to implement or use the present application. Various modifications made to the embodiments will be obvious to a person skilled in the art, and the general principles defined herein may be implemented in other embodiments without departing from the spirit or scope of the present application. Therefore, the present application is not intended to be limited to the embodiments illustrated herein, but shall be construed in the widest scope consistent with the principles and novel features disclosed herein.

What is claimed is:

1. An image matching method, comprising:
    acquiring a first image sequence and a second image sequence, wherein the first image sequence and the second image sequence are image frame sequences acquired for a same object;
    acquiring a first object and a second object, wherein the first object is an object reconstructed using the first image sequence, and the second object is an object reconstructed using the second image sequence;
    performing registration of the first object and the second object to obtain a registration result, wherein the registration result comprises a one-to-one correspondence between any pixel point on the first object and a pixel point on the second object;
    acquiring a mapping relationship according to the registration result, wherein the mapping relationship is configured to indicate a correspondence between an image frame in the first image sequence and an image frame in the second image sequence; and
    displaying a matching image frame correspondingly according to the mapping relationship in case of displaying a target image frame in the first image sequence, wherein the matching image frame is an image frame in the second image sequence corresponding to the target image frame, and the target image frame is any image frame in the first image sequence.

2. The method according to claim 1, wherein the acquiring a first image sequence and a second image sequence comprises:
receiving the first image sequence; and
acquiring an image sequence having a same identification with the first image sequence from historical image sequences as the second image sequence.

3. The method according to claim 2, wherein the receiving the first image sequence comprises:
acquiring the first image sequence from an image sequence imaging device, in case of the image sequence imaging device generating the first image sequence.

4. The method according to claim 3, wherein the performing registration of the first object and the second object to obtain a registration result comprises:
dividing the first object and the second object into multiple parts respectively;
pairing vertices of a first circumscribed polyhedron and a second circumscribed polyhedron to obtain matching points, wherein the first circumscribed polyhedron is a circumscribed polyhedron of each part obtained by dividing the first object, and the second circumscribed polyhedron is a circumscribed polyhedron of each part obtained by dividing the second object;
determining a registration matrix equation according to the matching points; and
solving the registration matrix equation by using a least square method to obtain the registration result.

5. The method according to claim 1, further comprising:
acquiring first lesion information and second lesion information, wherein the first lesion information represents diagnosis information of a lesion obtained based on the first image sequence, and the second lesion information represents diagnosis information of a lesion obtained based on the second image sequence; and
displaying contents of same items in the first lesion information and the second lesion information correspondingly.

6. The method according to claim 1, further comprising:
acquiring a second frame identification, wherein the second frame identification is an identification of an image frame in which a lesion is located in the second image sequence; and
determining a first frame identification according to the second frame identification and the mapping relationship, wherein the first frame identification is an identification of an image frame in which a lesion is located in the first image sequence, and acquisition time of the first image sequence is later than that of the second image sequence.

7. An image matching device, comprising:
a processor; and
a memory for storing programs executable by the processor,
wherein the processor is configured to:
acquire a first image sequence and a second image sequence, wherein the first image sequence and the second image sequence are image frame sequences acquired for a same object;
acquire a first object and a second object, wherein the first object is an object reconstructed using the first image sequence, and the second object is an object reconstructed using the second image sequence;
perform registration of the first object and the second object to obtain a registration result, wherein the registration result comprises a one-to-one correspondence between any pixel point on the first object and a pixel point on the second object;
acquire a mapping relationship according to the registration result, wherein the mapping relationship is configured to indicate a correspondence between an image frame in the first image sequence and an image frame in the second image sequence; and
display a matching image frame correspondingly according to the mapping relationship in case of displaying a target image frame in the first image sequence, wherein the matching image frame is an image frame in the second image sequence corresponding to the target image frame, and the target image frame is any image frame in the first image sequence.

8. The device according to claim 7, wherein the processor is configured to:
receive the first image sequence; and
acquire an image sequence having a same identification with the first image sequence from historical image sequences as the second image sequence.

9. The device according to claim 8, wherein the processor is configured to acquire the first image sequence from an image sequence imaging device, in case of the image sequence imaging device generating the first image sequence.

10. The device according to claim 9, wherein the processor is configured to:
divide the first object and the second object into multiple parts respectively;
pair vertices of a first circumscribed polyhedron and a second circumscribed polyhedron to obtain matching points, wherein the first circumscribed polyhedron is a circumscribed polyhedron of each part obtained by dividing the first object, and the second circumscribed polyhedron is a circumscribed polyhedron of each part obtained by dividing the second object;
determine a registration matrix equation according to the matching points; and
solve the registration matrix equation by using a least square method to obtain the registration result.

11. The device according to claim 7, wherein the processor is further configured to:
acquire first lesion information and second lesion information, wherein the first lesion information represents diagnosis information of a lesion obtained based on the first image sequence, and the second lesion information represents diagnosis information of a lesion obtained based on the second image sequence; and
display contents of same items in the first lesion information and the second lesion information correspondingly.

12. The device according to claim 7, wherein the processor is further configured to:
acquire a second frame identification, wherein the second frame identification is an identification of an image frame in which a lesion is located in the second image sequence; and
determine a first frame identification according to the second frame identification and the mapping relationship, wherein the first frame identification is an identification of an image frame in which a lesion is located in the first image sequence, and acquisition time of the first image sequence is later than that of the second image sequence.

13. A non-transitory storage medium, wherein the storage medium stores computer programs, and when executed by a processor, the computer programs cause the processor to implement an image matching method, the image matching method comprising:
- acquiring a first image sequence and a second image sequence, wherein the first image sequence and the second image sequence are image frame sequences acquired for a same object;
- acquiring a first object and a second object, wherein the first object is an object reconstructed using the first image sequence, and the second object is an object reconstructed using the second image sequence;
- performing registration of the first object and the second object to obtain a registration result, wherein the registration result comprises a one-to-one correspondence between any pixel point on the first object and a pixel point on the second object;
- acquiring a mapping relationship according to the registration result, wherein the mapping relationship is configured to indicate a correspondence between an image frame in the first image sequence and an image frame in the second image sequence; and
- displaying a matching image frame correspondingly according to the mapping relationship in case of displaying a target image frame in the first image sequence, wherein the matching image frame is an image frame in the second image sequence corresponding to the target image frame, and the target image frame is any image frame in the first image sequence.

* * * * *